(12) United States Patent
Bao et al.

(10) Patent No.: US 11,359,177 B2
(45) Date of Patent: Jun. 14, 2022

(54) **C6/C5 CO-FERMENTED *SACCHAROMYCES CEREVISIAE* CAPABLE OF RELIEVING ANTAGONISM BETWEEN HIGH XYLOSE UTILIZATION AND HIGH ROBUSTNESS AND APPLICATION THEREOF**

(71) Applicant: Qilu University of Technology, Jinan (CN)

(72) Inventors: Xiaoming Bao, Jinan (CN); Jianzhi Zhao, Jinan (CN); Fangqing Wei, Jinan (CN); Hongxing Li, Jinan (CN); Zailu Li, Jinan (CN)

(73) Assignee: QILU UNIVERSITY OF TECHNOLOGY, Jinan (CN)

( * ) Notice: Subject to any disclaimer, the term of this patent is extended or adjusted under 35 U.S.C. 154(b) by 0 days.

(21) Appl. No.: 17/401,688

(22) Filed: Aug. 13, 2021

(65) Prior Publication Data
US 2022/0154131 A1   May 19, 2022

(30) Foreign Application Priority Data
Nov. 18, 2020 (CN) .......................... 202011296559.5

(51) Int. Cl.
*C12N 1/18* (2006.01)
*C12P 7/10* (2006.01)
*C12N 15/01* (2006.01)
*C12R 1/865* (2006.01)

(52) U.S. Cl.
CPC ............. *C12N 1/185* (2021.05); *C12N 15/01* (2013.01); *C12P 7/10* (2013.01); *C12R 2001/865* (2021.05)

(58) Field of Classification Search
CPC . C12N 1/185; C12N 15/01; C12P 7/10; C12P 7/06
See application file for complete search history.

(56) References Cited

U.S. PATENT DOCUMENTS

2021/0222210 A1\* 7/2021 Luo ........................ C12N 1/185

OTHER PUBLICATIONS

CN 202011296559.5—Notice of Allowance, dated May 26, 2021, 3 pages, (with English translation).

\* cited by examiner

*Primary Examiner* — Maryam Monshipouri
(74) *Attorney, Agent, or Firm* — Getech Law LLC; Jun Ye (57) ABSTRACT

The present invention further discloses an application of *Saccharomyces cerevisiae* in the fermentation of a second generation fuel, ethanol, with a straw lignocellulose biomass hydrolysate as a raw material. Experiments prove that the strain of the prevent invention has an efficient co-fermentation capacity of C6/C5 while tolerating multiple inhibitors, and can consume all the glucose and xylose to produce ethanol; and the sugar-alcohol conversion rate is up to 0.43 g $g^{-1}$. The strain and screening strategy used in the present invention provide technical reference and basis for the further breeding of a *Saccharomyces cerevisiae* strain which has a superior fermenting property and is produced by the second generation fuel, ethanol.

4 Claims, 5 Drawing Sheets

C6/C5 CO-FERMENTED *SACCHAROMYCES CEREVISIAE* CAPABLE OF RELIEVING ANTAGONISM BETWEEN HIGH XYLOSE UTILIZATION AND HIGH ROBUSTNESS AND APPLICATION THEREOF

TECHNICAL FIELD

The present invention relates to C6/C5 co-fermented *Saccharomyces cerevisiae* capable of relieving antagonism between high xylose utilization and high robustness and an application thereof, belonging to the field of biotechnology.

BACKGROUND

Lignocellulose biomass is the richest renewable energy source on the earth with an annual output of exceeding $10^{13}$ tons. With the increasingly exhausted petrifaction resources and environmental pollution problem, to develop a biomass energy technology with lignocellulose biomass as a raw material is one of the important measures to achieve energy transformation, and is also an important part of the new energy structure around the world. Lignocellulose biomass serves as a raw material to produce clean liquid fuels and chemicals by the transformation of a microbial cell factory, which is an important path of the biomass energy technology. Lignocellulose is difficultly utilized by microorganism directly due to a firm and compact chemical structure. Therefore, it needs to perform necessary hydrolysis on raw materials, thus releasing sugar components capable of being directly utilized by microorganism. However, the chemical component of lignocellulose hydrolysate is relatively complicated and contains hexose, pentose and other sugar components, as well as weak acids, furans, phenols and other non-sugar inhibitor components. The non-sugar inhibitor components generally have inhibiting effects on the growth and metabolism of fermentation microorganisms. Therefore, based on the characteristics of the components of the lignocellulose hydrolysate, fermentation microorganism must have two characteristics on performance, namely, an efficient hexose/pentose co-fermentation capability and higher inhibitor robustness.

The second generation fuel, ethanol, is ethanol produced with lignocellulose as raw material, and is one of the ideal liquid fuels to replace fossil energy acknowledged internationally. As a major fermentation microorganism produced by ethanol, *Saccharomyces cerevisiae* is considered as one of the most potential industrial strains to transform lignocellulose hydrolysates to produce fuel ethanol due to its powerful fermentation capacity of hexose and robustness, and mature gene manipulation technology. However, the wild-type *Saccharomyces cerevisiae* has extremely weak pentose metabolic capability only due to lack of a critical approach of pentose (e.g., xylose) metabolism. Xylose is a kind of pentose having the second-highest content in lignocellulose biomass; and whether of utilizing xylose efficiently is one of the key links to improve the transformation efficiency of raw material substrates and the economic profitability of fuel ethanol. To improve the xylose utilization capacity of *Saccharomyces cerevisiae*, domestic and overseas scientists have conducted lots of works, mainly including: 1) heterologous introduction of initial metabolic pathways of xylose, namely, xylose reductase-xylitol dehydrogenase (XR-XDH) pathway and xylose isomerase pathway; 2) optimization of intrinsic metabolic pathway of xylose; 3) optimization of metabolic balance of intracellular cofactors; 4) specific and efficient screening of xylose translocators; and 5) adaptive evolution engineering and the like. Through researchers' unremitting efforts, the metabolic capability of xylose, the purified product of *Saccharomyces cerevisiae*, has been basically up to the metabolic level of glucose. *Saccharomyces cerevisiae* has the capacity of co-utilizing glucose and xylose, but still has lower resistance to inhibitors in xylose lignocellulose. The inhibitor robustness is also an important factor to influence the growth and metabolic efficiency of microorganisms. In recent ten years, scientists have improved the resistance of cells to a single inhibitor to some extent by transforming the resistance response pathway of intracellular inhibitors and other rational transformation strategies, as well as random mutation, adaptive evolution and other non-rational strategies. Furthermore, for the synergistic inhibition effect of a plurality of inhibitors in lignocellulose hydrolysate, a mixed inhibitor having a lower concentration also shows stronger inhibiting effect. During research process, domestic and overseas researchers including the applicant team have found that *Saccharomyces cerevisiae* has declined xylose metabolic capability in different levels while improving the inhibitor resistance; it seems that there is a antagonism relationship between such two characters. Therefore, to obtain such two characters of high xylose metabolism and high robustness in cells brings a big challenge to the screening of a strain producing the second generation fuel, ethanol.

In preliminary work, the applicant has constructed a recombinant *Saccharomyces cerevisiae* strain co-utilizing glucose/xylose efficiently through rational metabolic engineering and adaptive evolution engineering based on a high-activity xylose isomerase screened from a metagenome of bovine rumen and a specific xylose transporter MGT05196N360F from *Meyerozyma guilliermondii*; but the strain has poor robustness in a cornstalk hydrolysate containing higher concentration of inhibitors. By experiments, the applicant has found that during the study of improving the robustness of the strain to inhibitors, when robustness is improved, but xylose metabolism obviously decreases, the above-mentioned antagonism relationship appears again. Through retrieval, there is no report of a related patent and literature on eliminating or relieving such a antagonism in *Saccharomyces cerevisiae* at present directed to the antagonism between xylose metabolism and robustness in strains.

SUMMARY

Directed to the problems of the insufficient resistance of a *Saccharomyces cerevisiae* strain produced by the second generation fuel ethanol to a mixed inhibitor in lignocellulose hydrolysate, and the antagonistic phenomenon between the inhibitor resistance and xylose metabolism capability in strains, the problem to be mainly solved by the present invention is to provide a C6/C5 co-fermented *Saccharomyces cerevisiae* strain capable of relieving antagonism between high xylose utilization and high robustness and an application thereof.

The C6/C5 co-fermented *Saccharomyces cerevisiae* capable of relieving antagonism between high xylose utilization and high robustness of the present invention, is characterized in that the strain simultaneously has the properties of high inhibitor robustness and high xylose utilization, and named *Saccharomyces cerevisiae* 6M-15; and the strain has been deposited on Aug. 17, 2020 at "China General Microbiological Culture Collection Center" (CGMCC) with the address of No. 3 of No. 1 Yard, West Beichen Road, Chaoyang District, Beijing and under the accession number: CGMCC No. 20436.

The above *Saccharomyces cerevisiae* 6M-15 is obtained by iterative mutagenesis at atmospheric pressure and room temperature plasma (ARTP) and in combination with alternative domestication and screening in a high-toxicity (containing a plurality of inhibitors) cornstalk pretreating fluid and a pure xylose medium; and the specific technical steps are as follows:

(1) Growth Test of an Original Strain in a High-Toxicity Cornstalk Pretreating Fluid:

The original strain is a C6/C5 co-fermented *Saccharomyces cerevisiae* strain LF1 constructed at earlier stage of the applicant's laboratory; and the strain has been applied for a patent with the application number: 201510747241.7 and accession number: CGMCC No. 11331.

Major sugar components in the high-toxicity cornstalk pretreating stock fluid (hereinafter referred to as a pretreating fluid) are glucose and xylose (concentrations are respectively 14 g $L^{-1}$ and 43 g $L^{-1}$); and the major inhibitors are acetic acid, 5-hydroxymethyl furfural, furfural and total phenolic compounds (concentrations are respectively 3.5 g $L^{-1}$, 2.7 g $L^{-1}$, 0.3 g $L^{-1}$ and 3.3 g $L^{-1}$).

Different ratios of pretreating fluid are added to aYP medium to survey the influence on the strain growth. Results show that when the pretreating fluid has an adding proportion of 50% (v/v), the strain growth is obviously inhibited, indicating that the inhibitor concentration in the 50% (v/v) pretreating fluid can cause obvious toxicity to cells. Based on this, the adding amount of the 50% (v/v) pretreating fluid can be determined as a selection pressure condition for the follow-up screening of a strain having improved inhibitor robustness.

(2) ARTP Mutagenesis:

First, a fatality rate curve of the original strain LF1 mutagenized by ARTP is drawn. Afterwards, LF1 is mutagenized according to the fatality rate, and the mutagenized bacterial cells are put on a YPD medium and incubated for 30 min for recovery growth. Finally, the bacterial cells are put on a YP medium containing 50% (v/v) pretreating fluid for domesticated culture for consecutive 30 d.

(3) Screening of the Strain Having Significantly Improved Robustness:

A proper amount of the above domesticated bacterial culture solution is taken, washed by sterile water and coated onto a YP solid medium containing 50% (v/v) pretreating fluid for culture. Several single colonies with larger diameter are picked; and a Bioscreen full-automatic growth curve analyzer is used to test the growing ability of the above colonies on the 50% (v/v) pretreating fluid medium. Strains growing faster are screened again under a same condition of a 40 mL medium to obtain the strains having the highest robustness, named LF1-6.

(4) Multi-Round Iterative Mutagenesis to Relieve the Antagonistic Phenomenon Between Xylose Utilization and Robustness:

The screened strain LF1-6 has significantly improved robustness, but has declined xylose utilization capacity. To restore the xylose utilization capacity of the strain, strains are subjected multi-round iterative mutagenesis, anaerobic culture on a pure xylose solid medium, then single colonies growing faster are picked to test the xylose utilization capacity, thus finally obtaining a C6/C5 co-fermented *Saccharomyces cerevisiae* strain capable of obviously relieving the antagonistic phenomenon between xylose utilization and robustness, named *Saccharomyces cerevisiae* 6M-15.

Provided is an application of the C6/C5 co-fermented *Saccharomyces cerevisiae* capable of relieving antagonism between high xylose utilization and high robustness in the fermentation of a second generation fuel, ethanol, with a straw lignocellulose biomass hydrolysate as a raw material.

In the above application, the method for shake-flask fermentation of a second generation fuel, ethanol with a straw lignocellulose biomass hydrolysate as a raw material is as follows:

water in a YP medium is replaced with a cornstalk hydrolysate, such that the fermentation medium has the following concentrations of components: 20 g $L^{-1}$ peptone, 10 g $L^{-1}$ yeast powder, 50.23±0.39 g L-1 glucose, 25.62±0.47 g $L^{-1}$ xylose, 0.93±0.13 g $L^{-1}$ cellobiose, 1.03±0.31 g $L^{-1}$ galactose, 8.09±0.24 g $L^{-1}$ arabinose, 4.36±0.28 g $L^{-1}$ acetic acid, 1.09±0.25 g $L^{-1}$ 5-hydroxymethyl furfural, 0.35±0.06 g $L^{-1}$ furfural, and 4.78±0.13 g $L^{-1}$ total phenol compounds, pH=3.5±0.2; and the fermentation conditions are as follows: a culture temperature is 30±2° C., a charging ratio is subjected to charging a 40 mL medium in a 150 mL oxygen-limiting flask, a shaker speed is 200±20 rpm; a rubber plug is used for sealing, a syringe needle is inserted to control the oxygen-limited conditions; an initial inoculation OD value is 10; all the glucose and xylose are completely consumed after culturing for 96±10 h under oxygen-limited conditions; a fermentation product is centrifuged and filtered to obtain a supernatant containing ethanol.

Further preferably, the method for shake-flask fermentation of a second generation fuel, ethanol with a straw lignocellulose biomass hydrolysate as a raw material is as follows:

water in a YP medium is replaced with a cornstalk hydrolysate, such that the fermentation medium has the following concentrations of components: 20 g $L^{-1}$ peptone, 10 g $L^{-1}$ yeast powder, 50 g L-1 glucose, 25 g $L^{-1}$ xylose, 0.93 g $L^{-1}$ cellobiose, 1.03 g $L^{-1}$ galactose, 8.09 g $L^{-1}$ arabinose, 4.36 g $L^{-1}$ acetic acid, 1.09 g $L^{-1}$ 5-hydroxymethyl furfural, 0.35 g $L^{-1}$ furfural, and 4.78 g $L^{-1}$ total phenol compounds, pH=3.5±0.1; and the fermentation conditions are as follows:

a culture temperature is 30° C., a charging ratio is subjected to charging a 40 mL medium in a 150 mL oxygen-limiting flask, a shaker speed is 200 rpm; a rubber plug is used for sealing, a syringe needle is inserted to control the oxygen-limited conditions; an initial inoculation OD value is 10; all the glucose and xylose are completely consumed after culturing for 96±1 h under oxygen-limited conditions; a fermentation product is centrifuged and filtered to obtain a supernatant containing ethanol.

Experiments prove that after all the glucose and xylose are completely consumed, the sugar-alcohol conversion rate is 0.43 g $g^{-1}$, up to 85% of the theoretical value.

The present invention discloses a *Saccharomyces cerevisiae* strain 6M-15 capable of relieving antagonism between high xylose utilization and high robustness; and the strain shows an excellent fermenting property in a cornstalk hydrolysate and thus, has a great potential of being applied in the industrial production of a second generation fuel, ethanol. The innovative point of the present invention is that the strain capable of possessing an efficient C6/C5 co-fermentation capacity while tolerating multi-inhibitors is finally obtained based on the antagonistic phenomenon between high xylose utilization and high robustness highlighting in the breeding process of the strain produced by a second generation fuel, ethanol, by an emerging ARTP mutation breeding technology, and in combination with anaerobic screening strategies and multi-round iterative mutagenesis and screening. Moreover, experiments prove that the strain 6M-15 provided by the present invention can consume all the glucose and xylose to generate ethanol having a sugar-alcohol conversion rate of 0.43 g g$^{-1}$. The strain and technical screening strategy used in the present invention provide technical reference and basis for the further breeding of a *Saccharomyces cerevisiae* strain which has a superior fermenting property and is produced by the second generation fuel, ethanol.

DETAILED DESCRIPTION OF THE EMBODIMENTS

The present invention will be further described in detail with reference to the specific drawings and examples. The examples below are merely preferred embodiments of the present invention. It should be indicated that the description below is merely for explaining the present invention, but not for limiting the present invention in any form. Any simple amendment, equivalent alteration and modification made to the embodiments on the basis of the technical spirit of the present invention shall fall within the scope of the technical solution of the present invention.

Unless otherwise specified, the materials, reagents and the like used in the examples are available commercially.

Example 1 Determination of Microbiological Media and Basic Culture Conditions (1) *Saccharomyces cerevisiae* Medium YP medium: 20 g L$^{-1}$ peptone and 10 g L$^{-1}$ yeast powder; YPD medium: 20 g L$^{-1}$ glucose was added to the YP medium; YPX medium: 40 g xylose was added to the YP medium; and YPGX medium: 40 g xylose and 80 g L$^{-1}$ glucose were added to the YP medium. YP medium containing pretreating fluid: different proportions of cornstalk pretreating fluid were added according to experiment demands; full-hydrolysate YP medium: water in the YP medium was replaced with hydrolysate. 20 g L$^{-1}$ g agar powder was added to the corresponding solid medium.

(2) Preparation of a Cornstalk Pretreating Fluid and Hydrolysate

Absolutely dry cornstalk was crushed into particles having a diameter of less than 1 mm, and 100 g straw particles were mixed with 0.5% dilute sulphuric acid according to a solid-to-liquid ratio of 1:5, then transferred to a stainless steel tube reactor, and heated up to 180° C. for reacting for 40 min, and the reaction mixture was centrifuged to obtain a supernatant, namely, the supernatant was the cornstalk pretreating fluid (hereinafter referred to as pretreating fluid).

The reaction mixture was transferred to a shake flask, and NaOH served to adjust pH to 4.8, 20 FPU/g cellulase was added for enzymolysis, where reaction temperature was 50° C., revolving speed was 200 rpm, enzymolysis time was 48 h; and the supernatant obtained by centrifugation was namely, the cornstalk hydrolysate (hereinafter referred to as hydrolysate).

Major sugar components of the pretreating fluid and hydrolysate, and concentration of the inhibitor were shown in Table 1.

Table 1 List of the components of the cornstalk pretreating fluid and hydrolysate (3) Basic Culture Conditions Culture conditions of oxygen-limited shake flask: culture temperature was 30° C.; 150 mL oxygen-limited flask was loaded with a 40 mL medium, shaker speed was 200 rpm and the shake flask was sealed by a rubber plug; a syringe needle was inserted to control the oxygen-limited conditions, three parallel fermentation experiments were performed, and sampling was performed for once per 4 h.

Culture conditions of the Bioscreen full-automatic growth curve analyzer: culture volume was 200 μL, initial inoculum size OD 600 was 0.2; culture temperature was 30° C., three parallel fermentation experiments were performed, and automatic sampling was performed to detect OD values per 0.5 h.

Example 2 Determination on the Detection Method of Raw Components and Fermentation Products The concentrations of the pretreating fluid, hydrolysate as well as substrate and product of ethanol during fermentation were measured by high performance liquid chromatography.

1 mL sample was taken and centrifuged at a high speed (13000 r/min, 5 min) to remove impurities or bacteria in the sample; supernatant was taken and filtered by a 0.22 μm microfiltration membrane; and the component content thereof was measured by a high performance liquid chromatography system Waters e2695. Standard sample concentration: 49.998 g L$^{-1}$ glucose, 48.891 g L$^{-1}$ xylose, 9.857 g L$^{-1}$ cellobiose, 6.029 g L$^{-1}$ galactose, 6.074 g L$^{-1}$ arabinose, 0.630 g L$^{-1}$ 5-hydroxymethyl furfural, and 1.042 g L$^{-1}$ furfural. Chromatographic conditions: ① glucose, xylose, arabinose, cellobiose, galactose, acetic acid and ethanol were analyzed by an HPX-87H ion-exchange chromatography (Bio-Rad Aminex); 5 mM $H_2SO_4$ served as a mobile phase of the chromatographic column at 45° C., and a Waters 2414RI differential refraction detector was used; ② furfural and 5-HMF were detected by a Waters 2998PDA UV detector and WondaSil C18 chromatographic column (GL Sciences) at 40° C. with 40% methanol as a mobile phase. The content of total phenols in the pretreating fluid was detected by a folin reagent; vanillic aldehyde served as a standard substance and was reacted with a Folin-Ciocalteu reagent to detect its absorption value at 725 nm.

Figure 1:
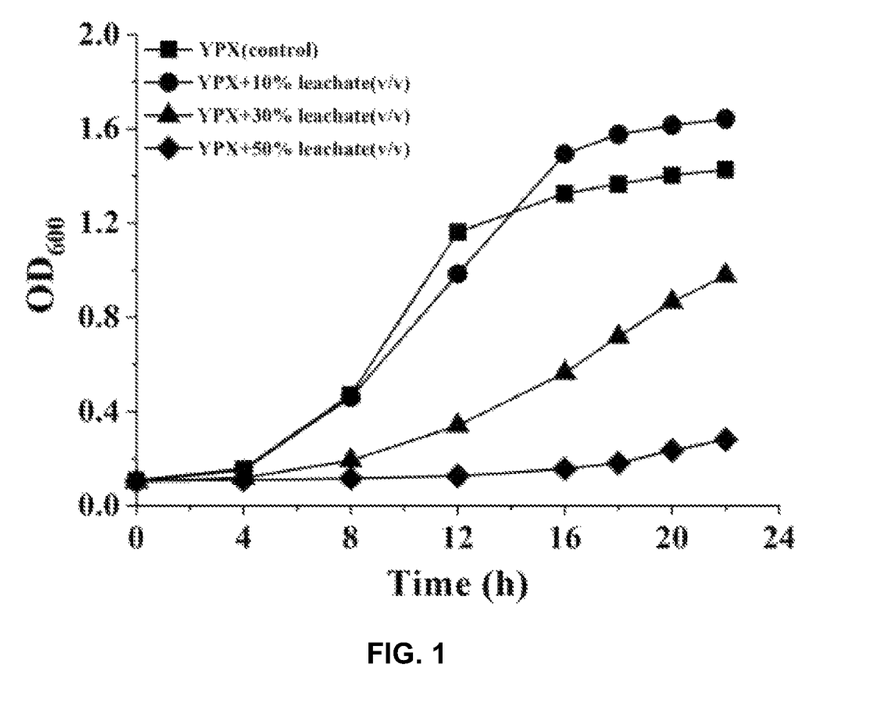
FIG. 1 shows growth situation of an original strain LF1 on a YP medium of a high-toxicity cornstalk pretreating fluid.

Example 3 Breeding of a C6/C5 Co-Fermented *Saccharomyces cerevisiae* Capable of Relieving Antagonism Between High Xylose Utilization and High Robustness Strain The original strain is a C6/C5 co-fermented *Saccharomyces cerevisiae* strain LF1 constructed by at an earlier stage of the applicant's laboratory; and the strain has been applied for a patent with the application number: 201510747241.7 and accession number: CGMCC No. 11331. The C6/C5 Co-fermented *Saccharomyces cerevisiae* capable of relieving antagonism between high xylose utilization and high robustness strain was expected to be obtained by iterative mutagenesis at atmospheric pressure and room temperature plasma (ARTP) and in combination with alternative domestication and screening in a high-toxicity (containing a plurality of inhibitors) cornstalk pretreating fluid and a pure xylose medium; and the specific technical steps were as follows:

(1) Determination on the Concentration of a High-Toxicity Cornstalk Pretreating Fluid Significantly Inhibiting Growth of an Original Strain Influences of the adding amount of the pretreating fluid in the medium on the growth of the original strain were tested. *Saccharomyces cerevisiae* YP media were respectively added 0% (control), 10%, 30%, and 50% (v/v) pretreating fluid; the original strain LF1 had an initial inoculation OD 600 of 0.2, an inoculation volume of 40 mL, culture temperature of 30° C., revolving speed of 200 rpm and culture time of 24 h. Results were shown in FIG. 1; when the pretreating fluid had an adding proportion of 50% (v/v), the strain growth was obviously inhibited. Based on this, the adding amount of the 50% (v/v) pretreating fluid could be determined as a pressure condition to screen a strain having improved inhibitor robustness in the follow-up experiments.

(2) ARTP Mutagenesis

① Test on the influences of different radiation time on the fatality rate of the original strain Single colonies of the original strain were picked and cultured to the mid-log phase, and centrifuged to collect bacteria solution, washed by sterile water for 2-3 times; a proper amount of solution was diluted to a bacterial suspension having an OD 600 value of 0.6-0.8; 10 μL bacterial suspension were taken and coated on a sterile metal slide glass; 4 time gradients, 0 s (control), 15 s, 30 s, and 45 s were configured in an ARTP mutation breeding apparatus, and 3 parallel samples were set to each gradient for mutagenesis. After all the samples were treated, slide glasses were respectively put to EP tubes loaded with 1 mL sterile water with sterile forceps, and oscillated for 5 min by a vibrator; then cells attached on the slide glass were eluted to sterile water to form a new bacterial suspension; then the new bacterial suspension was concentrated to 100 μL and completely coated on aYPD plate, cultured at 30° C.; after growing bacterial colonies, fatality rate was calculated according to the quantity variance of the bacterial colonies between the experimental group and control group.

Figure 2:
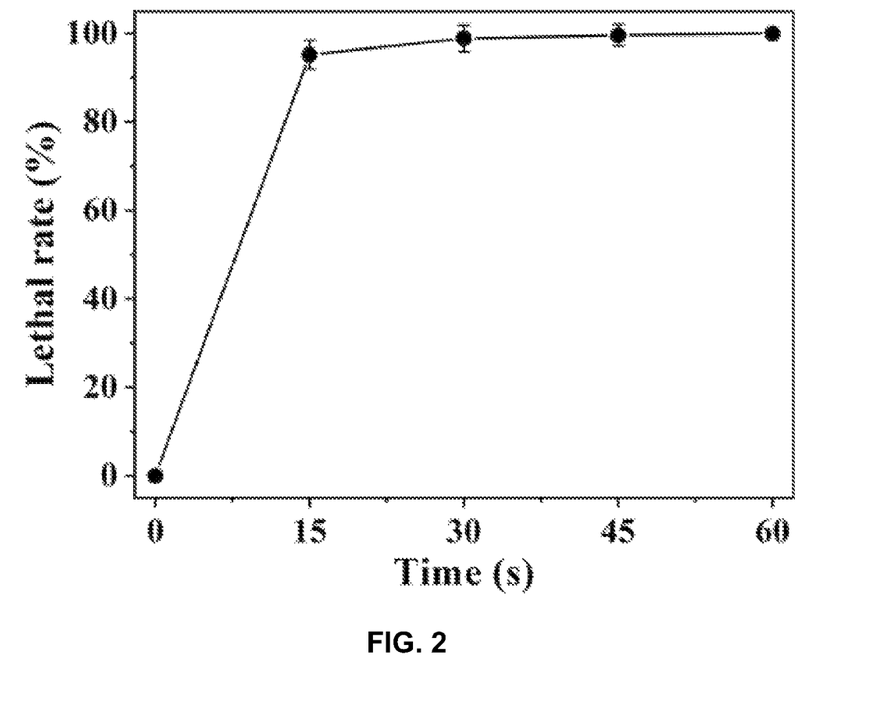
FIG. 2 shows fatality rate of the original strain LF1 mutagenized by ARTP.

② Determination of mutagenesis conditions After being irradiated for 15 s at 120 W power and 10 SLM gas flow, the original strain had a fatality rate of 97.2%; and when irradiated for 30 s, no strain survived (as shown in FIG. 2). Therefore, 15 s mutagenesis time, 120 W power and 10 SLM gas flow served as conditions of ARTP mutation breeding.

③ Based on the mutagenesis conditions determined in ②, the mutagenized original strain was put on a YPD medium and incubated for 30 min for recovery growth. Finally, the bacterial cells were put on a YP medium containing 50% (v/v) pretreating fluid for domesticated culture. The doubling of cell biomass served as a transfer indicator; after through the transferred incubation for domesticated culture for about 30 d, doubling time of the cell biomass significantly shortened and kept the same, cells were coated on a YP solid medium containing 50% (v/v) pretreating fluid to separate single colonies.

(3) Screening of the Strain Having Significantly Improved Robustness

Figure 3:
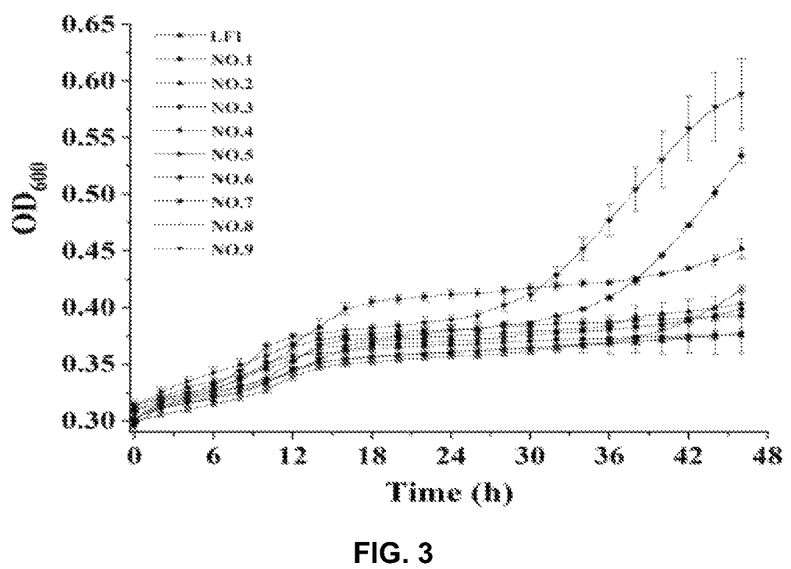
FIG. 3 shows a high-resistant mutant strain screened by Bioscreen.

Cells in (2)③ were coated on a YP solid medium containing 50% (v/v) pretreating fluid for culture at 30° C.; after bacterial colonies grew, bacterial colonies having a relatively large diameter were picked; and a Bioscreen full-automatic growth curve analyzer (Oy GrowthCurves Ab Ltd, Helsinki, Finland) was used to test the growth performance of the mutant strains on the YP medium containing 50% (v/v) pretreating fluid (as shown in FIG. 3); the culture volume was 200 μL; initial inoculum size OD 600 was 0.2; and culture temperature was 30° C. Strains growing faster were screened again under a same condition of a 40 mL medium to obtain a strain having the highest robustness, named LF1-6.

Figure 4:
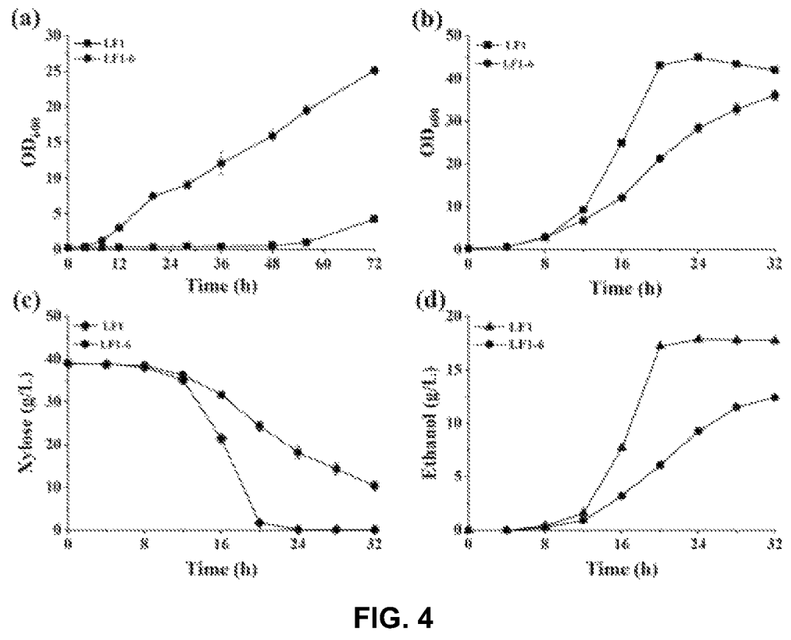
FIG. 4 shows oxygen-limited fermenting properties of different strains on a YP medium containing 50% (v/v) pretreating fluid and 40 g L$^{-1}$ YPX medium; (a) denotes growth of LF1 and LF1-6 on a YP medium containing 50% (v/v) pretreating fluid; (b) denotes growth of LF1 and LF1-6 on a YPX medium (40 g L$^{-1}$ xylose); (c) denotes ethanol consumption; and (d) denotes ethanol yield.
Figure 5:
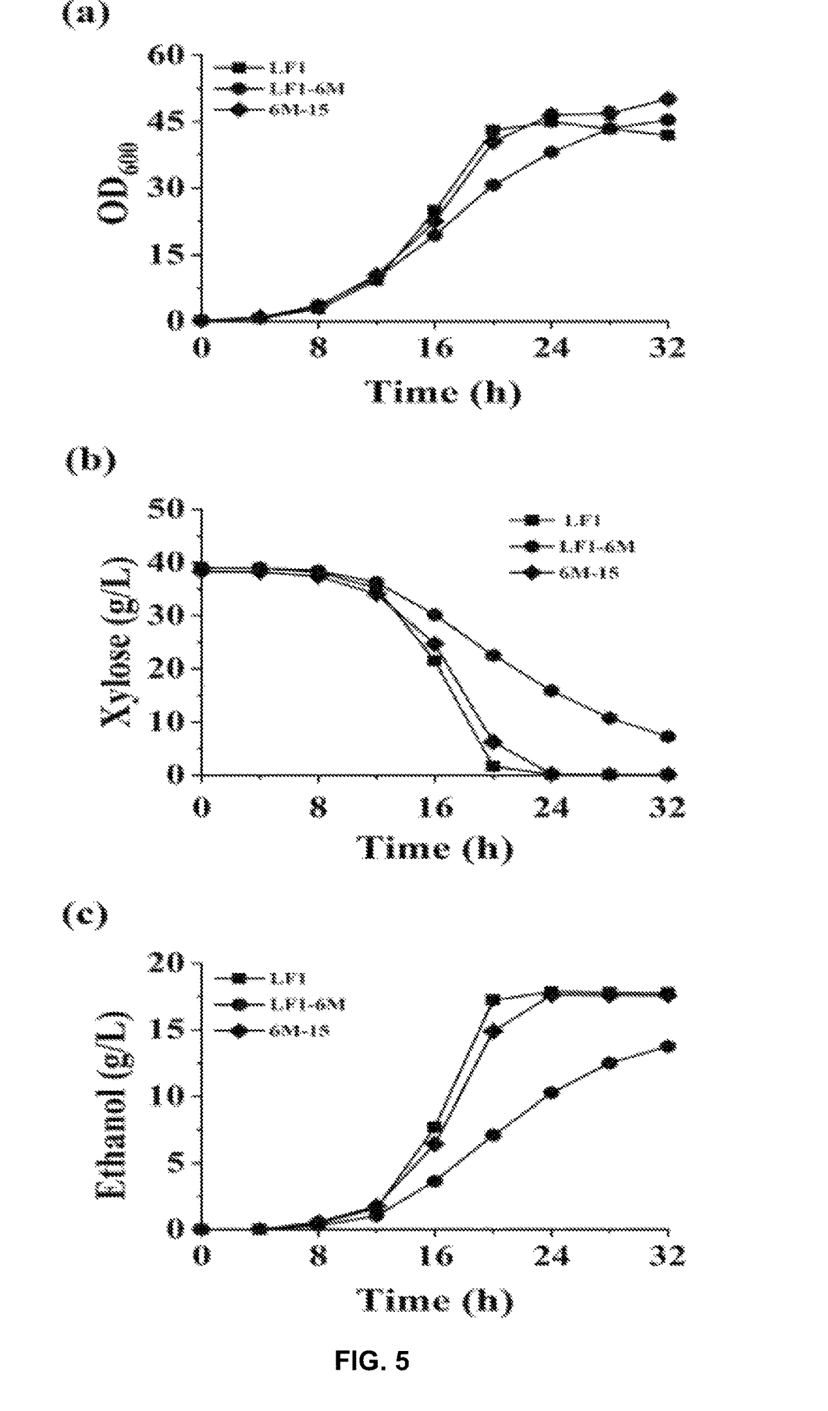
FIG. 5 shows oxygen-limited fermenting properties of the original strain LF1 and mutant strains LF1-6M and 6M-15 on the YPX medium (40 g xylose); (a) denotes strain growth; (b) denotes xylose metabolism; and (c) denotes ethanol yield.

Batch fermentation test was performed on the 50% (v/v) pretreating fluid medium; and fermentation conditions were as follows: culture temperature was 30° C.; 150 mL oxygen-limited flask was loaded with a 40 mL 50% (v/v) pretreating fluid medium; shaker speed was 200 rpm and the flask was sealed with a rubber plug; then a syringe needle was inserted to control the oxygen-limited conditions; initial inoculum size OD was 0.2; sampling was performed per 4 h; the fermentation experiment was repeated for three times; and a mean value of the data was taken for calculation. Results (as shown in FIG. 4a) showed that LF1-6 had significantly enhanced robustness, while almost no original strain grew. But on the 40 g $L^{-1}$ xylose medium, the xylose utilization rate (as shown in FIG. 4c) and ethanol generation rate (as shown in FIG. 4d) of the mutant strain LF1-6 were obviously lower than these of the original strain LF1; and there was an antagonism relationship between high xylose utilization and high robustness. The mutant strain LF1-6 was alternatively domesticated on the 50% (v/v) pretreating fluid medium and the pure xylose medium to screen a strain having improved xylose metabolic capability, named LF1-6M; and the strain was fermented for 20 h on the same xylose medium; the OD 600 improved 44.23%, xylose utilization rate improved 6.58%. But compared with the xylose utilization rate of the original strain LF1, there was still a big difference (42.4% vs 95.6%); the antagonism problem could be not solved effectively (as shown in FIGS. 5a and b).

(4) Screening of a Strain Relieving Antagonism Between Xylose Utilization and Robustness by Multi-Round Iterative ARTP Mutagenesis and Anaerobic Culture Directed to the above antagonism problem, LF1-6M, as an original strain, was subjected to multi-round iterative ARTP mutagenesis, and anaerobic culture on a pure xylose solid YPX medium; and alternatively domesticated on a YP medium containing 50% (v/v) pretreating fluid and YPX medium; the growth OD 600 value served as a detection indicator; when the strain was domesticated till the cell biomass doubled, the time significantly shortened and kept the same. A proper amount of the final bacterial suspension was coated on a YP medium containing 50% (v/v) pretreating fluid; after bacterial colonies grew, bacterial colonies having a larger diameter were picked to test the xylose utilization capacity and robustness; thus finally screening a mutant strain, namely, a strain having synchronously improved robustness and xylose metabolism, named *Saccharomyces cerevisiae* 6M-15; and the strain has been deposited on Aug. 17, 2020 at "China General Microbiological Culture Collection Center" (CGMCC) (address: No. 3 of No. 1 Yard, West Beichen Road, Chaoyang District, Beijing) under the accession number: CGMCC No. 20436.

Example 4 Comparison of the Fermenting Property and Ethanol Yield of Different Mutant Strains Between YPX and YPGX Media (1) Media: YPX medium: 20 g $L^{-1}$ peptone, 10 g $L^{-1}$ yeast powder, and 40 g $L^{-1}$ xylose; YPGX medium: 20 g $L^{-1}$ peptone, 10 g $L^{-1}$ yeast powder, 80 g $L^{-1}$ glucose, and 40 g xylose.

(2) Activation of strains: a single colony of a single strain to be tested was picked and inoculated on a 5 mL YPX fluid medium for culture for 24 h at 30° C. and 200 rpm; then transferred on a 10 mL YPX fluid medium for secondary activation for 12 h. Activated strains were respectively inoculated on 150 mL conical flasks containing 40 mL YPX and YPGX fluid media for fermentation culture.

(3) Fermentation conditions: culture temperature was 30° C.; 150 mL oxygen-limited flask was loaded with a 40 mL medium, shaker speed was 200 rpm and the flask was sealed by a rubber plug; a syringe needle was inserted to control the oxygen-limited conditions; initial inoculation OD value was 0.2, sampling was performed for once per 4 h to detect the OD value; and the sample was centrifuged and filtered to obtain a supernatant; the HPLC method in Example 2 was taken to detect the change of the sugar components and fermentation products; three parallel experiments were performed for each strain.

Figure 6:
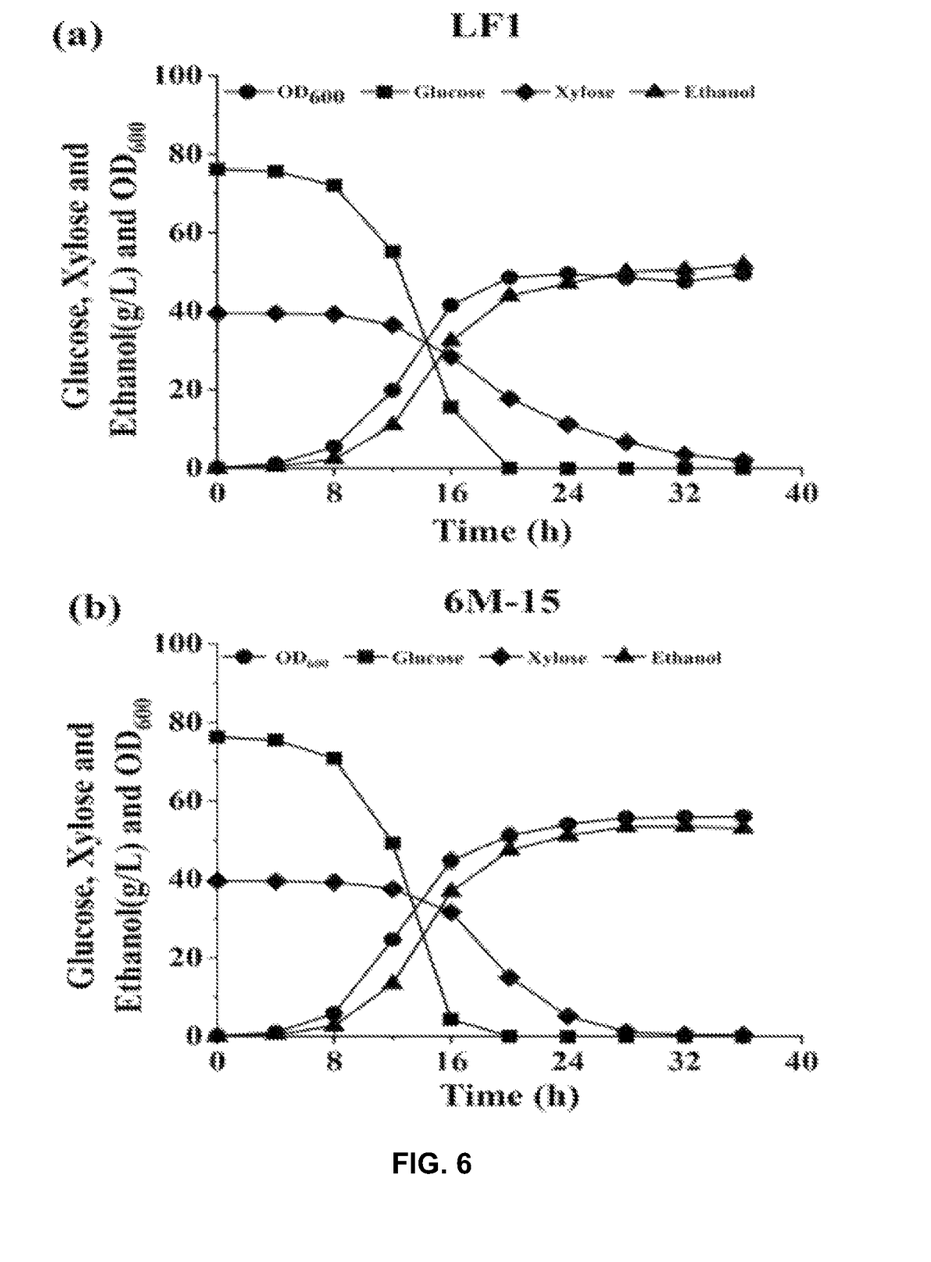
FIG. 6 shows oxygen-limited fermenting properties of the original strain LF1(a) and mutant strain 6M-15(b) on high-concentration mixed sugars (80 g L$^{-1}$ glucose and 40 g xylose).

The fermentation results showed as follows:

On a pure xylose YPX medium, the mutant strain had gradually improved xylose utilization capacity (as shown in FIG. 5), LF1≈6M-15>LF1-6M; 6M-15 could completely utilize xylose when fermented for 24 h, basically being up to the xylose metabolic level of the original strain LF1; and the sugar-alcohol conversion rate at the peak of ethanol yield was up to 90.98% of the theoretical value. Further, 6M-15 showed excellent fermenting properties (as shown in FIG. 6) on a mixed YPGX medium containing 80 g $L^{-1}$ glucose and 40 g $L^{-1}$ xylose. 6M-15 could completely consume the sugar components within 28 h; compared with the original strain, the fermentation time shortened 8 h (28 h vs 36 h); and the maximum ethanol concentration might be up to 54.98 g $L^{-1}$; and the sugar-alcohol conversion rate might be up to 91.37% of the theoretical value. It can be seen from the above results that the high-robustness strain had a recovered xylose metabolic capability through multi-round ARTP iterative mutagenesis and anaerobic screening.

Example 5 Ethanol Fermenting Properties of the Original Strain LF1 and Mutant Strain 6M-15 on a Cornstalk Hydrolysate YP Medium (1) Cornstalk hydrolysate YP medium: cornstalk hydrolysate was used to substitute the water in the YP medium (20 g $L^{-1}$ peptone and 10 g $L^{-1}$ yeast powder) Major sugar components and concentrations of the medium: 50 g $L^{-1}$ glucose and 25 g $L^{-1}$ xylose; as well as major inhibitors and concentrations: 4.36 g $L^{-1}$ acetic acid, 1.09 g 5-hydroxymethyl furfural, 0.35 g $L^{-1}$ furfural and 4.78 g $L^{-1}$ total phenol compounds, pH=3.5.

(2) The reactivation process of the strains was set forth in Example 4.

(3) Fermentation conditions were set forth in Example 4; initial inoculation OD value was 10; sampling was performed for once per 12 h; and the detection method was set forth in Example 2.

Figure 7:
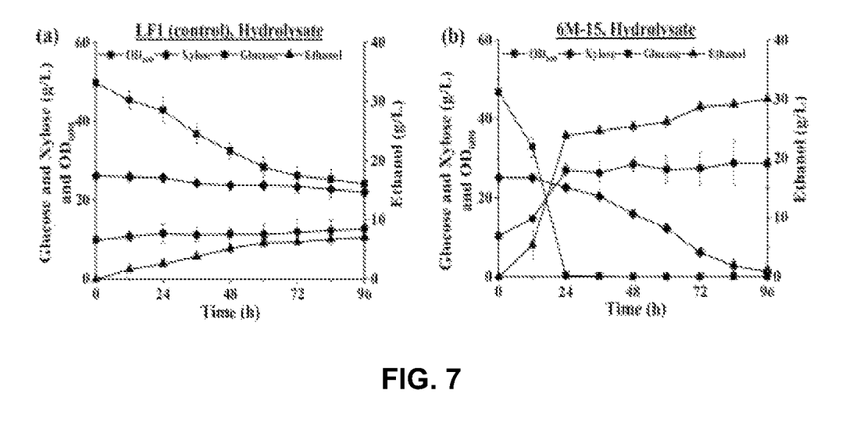
FIG. 7 shows oxygen-limited fermenting properties of the original strain LF1(a) and mutant strain 6M-15(b) on a YP medium of a non-detoxification cornstalk hydrolysate.

The fermentation results showed as follows:

In the fermentation process of a full hydrolysate YP medium having a low pH (about 3.5) and containing more higher concentration of inhibitors, the growth of the original strain LF1 was seriously inhibited; the glucose metabolic rate was slow; almost no xylose was utilized; at the end of the fermentation, LF1 only utilized 50% glucose, and only produced about 7.5 g ethanol. However, the growth of the mutant strain 6M-15 was almost not influenced; the glucose utilization rate was faster, all the glucose could be utilized within 24 h while utilizing xylose synchronously; at the end of the fermentation, 6M-15 might completely utilize glucose and xylose; ethanol yield was 30.53 g $L^{-1}$; sugar-alcohol conversion rate was 0.43 g $L^{-1}$, being up to 85% of the theoretical value (as shown in FIG. 7).

When concentrations of acetic acid, 5-hydroxymethyl furfural, furfural and total phenol compounds and other major inhibitors in the straw biological hydrolysate were not higher than the above concentration, and pH was not lower than 3.5, the strain had obvious growth vigor; and the ethanol yield produced through the transformation of glucose and xylose was not lower than 0.43 $g^{-1}$.

It can be seen from the above results that the mutant strain 6M-15 finally screened in the present invention simultaneously has the characteristics of high xylose utilization rate and high robustness to inhibitors in hydrolysate, thus significantly relieving the prominent antagonistic problem between high xylose utilization and high robustness in the breeding process of a *Saccharomyces cerevisiae* strain with lignocellulose biomass hydrolysate as a raw material to produce a second generation fuel, ethanol. To sum up, the breeding 6M-15 strain (accession number: CGMCC No. 20436) in the present invention has the ability of resisting multiple inhibitors in lignocellulose biomass hydrolysate while possessing a C6/C5 co-fermentation capacity. The strain is a potential strain applied to the industrial production of a second generation fuel, ethanol. Moreover, the strain provides excellent substrate cells for the further breeding of the *Saccharomyces cerevisiae* strain which has more excellent fermenting property and produced by the second generation fuel, ethanol.

Example 6 Application of the C6/C5 Co-Fermented *Saccharomyces cerevisiae* Capable of Relieving Antagonism Between High Xylose Utilization and High Robustness in the Fermentation of a Second Generation Fuel, Ethanol, with a Straw Lignocellulose Biomass Hydrolysate as a Raw Material The method for shake-flask fermentation of a second generation fuel, ethanol with a straw lignocellulose biomass hydrolysate as a raw material was as follows:

water in a YP medium was replaced with a cornstalk hydrolysate, such that the fermentation medium had the following concentrations of components: 20 g $L^{-1}$ peptone, 10 g $L^{-1}$ yeast powder, 50 g L-1 glucose, 25 g $L^{-1}$ xylose, 0.93 $L^{-1}$ cellobiose, 1.03 g $L^{-1}$ galactose, 8.09 g arabinose, 4.36 g L$^{-1}$ acetic acid, 1.09 g L$^{-1}$ 5-hydroxymethyl furfural, 0.35 g L$^{-1}$ furfural, and 4.78 g L$^{-1}$ total phenol compounds, pH=3.5±0.1; and the fermentation conditions were as follows: a culture temperature was 30° C., a charging ratio was subjected to charging a 40 mL medium in a 150 mL oxygen-limiting flask, a shaker speed was 200 rpm; a rubber plug was used for sealing, a syringe needle was inserted to control the oxygen-limited conditions; an initial inoculation OD value was 10; all the glucose and xylose were completely consumed after culturing for 96±1 h under oxygen-limited conditions; a fermentation product was centrifuged and filtered to obtain a supernatant containing ethanol.

Specific operating steps were set forth in Examples 4 and 5.

The invention claimed is:

1. An isolated yeast cell of a C6/C5 co-fermented *Saccharomyces cerevisiae*, deposited or identified as "China General Microbiological Culture Collection Center" accession number: CGMCC No. 20436, wherein, the isolated yeast cell is able to relieve antagonism between high inhibitor robustness and high xylose utilization during fermentation under ethanol producing conditions.

2. The isolated yeast cell of a C6/C5 co-fermented *Saccharomyces cerevisiae* of claim 1, wherein the fermentation under ethanol producing conditions includes a straw lignocellulose biomass hydrolysate as a raw material.

3. A method of fermentation of the isolated yeast cell of a C6/C5 co-fermented *Saccharomyces cerevisiae*, deposited or identified as "China General Microbiological Culture Collection Center" accession number: CGMCC No. 20436, wherein, the isolated yeast cell is able to relieve antagonism between high inhibitor robustness and high xylose utilization during fermentation under ethanol producing conditions to induce ethanol production by the cells, wherein said fermentation method comprises of:

(a) providing a fermentation medium, wherein the pH is in the range of 3.3 to 3.7, said fermentation medium comprising of: peptone at about 20 gL$^{-1}$, yeast extract at about 10 gL$^{-1}$, glucose in the range of 49.84 to 50.62 gL$^{-1}$, xylose in the range of 25.15 to 26.09 gL$^{-1}$, cellobiose in the range of 0.8 to 1.06 gL$^{-1}$, galactose in the range of 0.72 to 1.34 gL$^{-1}$, arabinose in the range of 7.85 to 8.33 gL$^{-1}$, acetic acid in the range of 4.08 to 4.64 gL$^{-1}$, 5-hydroxymethyl furfural in the range of 0.84 to 1.34 gL$^{-1}$, furfural in the range of 0.29 to 0.41 gL$^{-1}$, and phenol compounds in the range of 4.65 to 4.91 gL$^{-1}$, wherein the phenol compounds are degradation products of lignin components from the lignocellulose raw materials, which include, but are not limited to para-hydroxyphenyl, guaiacyl or syringyl, vanillin, guaiacol, p-hydroxybenzoic acid, and p-coumaric acid; and (b) fermenting the isolated yeast cell using a straw lignocellulose biomass hydrolysate as a raw material, wherein the fermentation temperature is in the range of 28 to 32° C.;
the fermenting comprising;
charging 40 mL fermentation medium in a 150 mL oxygen-limited flask;
shaking the flask in a shaker at a speed in the range of 180 to 220 rpm;
sealing the flask using a rubber plug; controlling the oxygen-limited conditions in the flask using a syringe needle;
inoculating the fermentation medium at initial optical density value to 10;
fermenting for a time period in the range of 86 to 106 hours under oxygen-limited conditions, wherein the glucose and xylose are completely consumed;
centrifuging and filtering the fermentation product to obtain a supernatant containing ethanol.

4. A method of fermentation of the isolated yeast cell of a C6/C5 co-fermented *Saccharomyces cerevisiae*, deposited or identified as "China General Microbiological Culture Collection Center" accession number: CGMCC No. 20436, wherein, the isolated yeast cell is able to relieve antagonism between high inhibitor robustness and high xylose utilization during fermentation under ethanol producing conditions to induce ethanol production by the cells, wherein said fermentation method comprises of:

(a) charging 40 mL of a fermentation medium in a 150 mL oxygen limited flask, wherein the pH of the fermentation medium is in the range of 3.3 to 3.7, and the temperature of the fermentation medium is at about 40° C., said fermentation medium comprising of:
peptone at about 20 gL$^{-1}$, yeast extract at about 10 gL$^{-1}$, glucose at about 50 gL$^{-1}$, xylose at about 25 gL$^{-1}$, cellobiose at about 0.93 gL$^{-1}$, galactose at about 1.03 gL$^{-1}$, arabinose 8.09 gL$^{-1}$, acetic acid 4.36 gL$^{-1}$, 5-hydroxymethyl furfural 1.09 gL$^{-1}$, furfural at about 0.35 gL$^{-1}$ and phenol compounds at about 4.78 gL$^{-1}$, wherein the phenol compounds are degradation products of lignin components from the lignocellulose raw materials, which include, but are not limited to para-hydroxyphenyl, guaiacyl or syringyl, vanillin, guaiacol, p-hydroxybenzoic acid, and p-coumaric acid; and (b) fermenting the isolated yeast cell using a straw lignocellulose biomass hydrolysate as a raw material comprising:
shaking the flask in a shaker at a speed of about 200 rpm;
sealing the flask using a rubber plug;
controlling the oxygen-limited conditions in the flask using a syringe needle;
inoculating the fermentation medium with said C6/C5 co-fermented *Saccharomyces cerevisiae* at initial optical density value to 10;
fermenting for a time period in the range of 95 to 97 hours under oxygen-limited conditions, wherein the glucose and xylose are completely consumed;
centrifuging and filtering the fermentation product to obtain a supernatant containing ethanol.

\* \* \* \* \*